US00PP22048P2

(12) United States Plant Patent
Salman

(10) Patent No.: US PP22,048 P2
(45) Date of Patent: Jul. 26, 2011

(54) ***BOUTELOUA* GRASS PLANT NAMED 'BLONDE AMBITION'**

(50) Latin Name: *Bouteloua gracilis*
Varietal Denomination: Blonde Ambition

(76) Inventor: David Salman, Santa Fe, NM (US)

( * ) Notice: Subject to any disclaimer, the term of this patent is extended or adjusted under 35 U.S.C. 154(b) by 0 days.

(21) Appl. No.: 12/800,261

(22) Filed: May 12, 2010

(51) Int. Cl.
*A01H 5/00* (2006.01)

(52) U.S. Cl. ..... Plt./384

(58) Field of Classification Search ..... Plt./384
See application file for complete search history.

*Primary Examiner* — Annette Para

(74) *Attorney, Agent, or Firm* — Holme Roberts & Owen LLP

(57) ABSTRACT

This invention relates to a new and distinct variety of *Bouteloua* grass plant named 'Blonde Ambition', which is primarily characterized by flower heads that emerge with a distinctive chartreuse color and age to a blonde color as the spikelets mature and a tall plant habit at maturity, is disclosed.

2 Drawing Sheets

Genus and species: *Bouteloua gracilis.*
Variety denomination: 'Blonde Ambition'.

BACKGROUND OF THE NEW PLANT

The present invention relates to a new and distinct blue grama grass plant designated 'Blonde Ambition' and botanically known as *Bouteloua gracilis*. This new blue grama grass originated from a whole plant mutation from a 'Hatchite' blue grama grass (unpatented) found in a residential yard in July 2007 in Santa Fe, N. Mex. 'Blonde Ambition' was first propagated asexually by crown divisions in August of 2007 in Santa Fe, N. Mex. and has been asexually propagated over six generations. The present invention has been found to be stable and reproduce true to type through successive asexual propagations via crown divisions.

Plant Breeder's Rights for this variety have not been applied for. 'Blonde Ambition' has not been made publicly available or sold more than one year prior to filing of this application.

SUMMARY OF THE INVENTION

The following are the most outstanding and distinguishing characteristics of this new cultivar when grown under normal horticultural practices in Santa Fe, N. Mex.

1. The flower head emerges with a distinctive chartreuse color and ages to blonde as the seeds mature; and
2. A tall plant habit at maturity.

DESCRIPTION OF THE PHOTOGRAPHS

This new blue grama grass plant is illustrated by the accompanying photographs, which were taken in Santa Fe, N. Mex. on an approximately two-year-old plant in August and September of 2009.

DESCRIPTION OF THE NEW VARIETY

Figure 1:
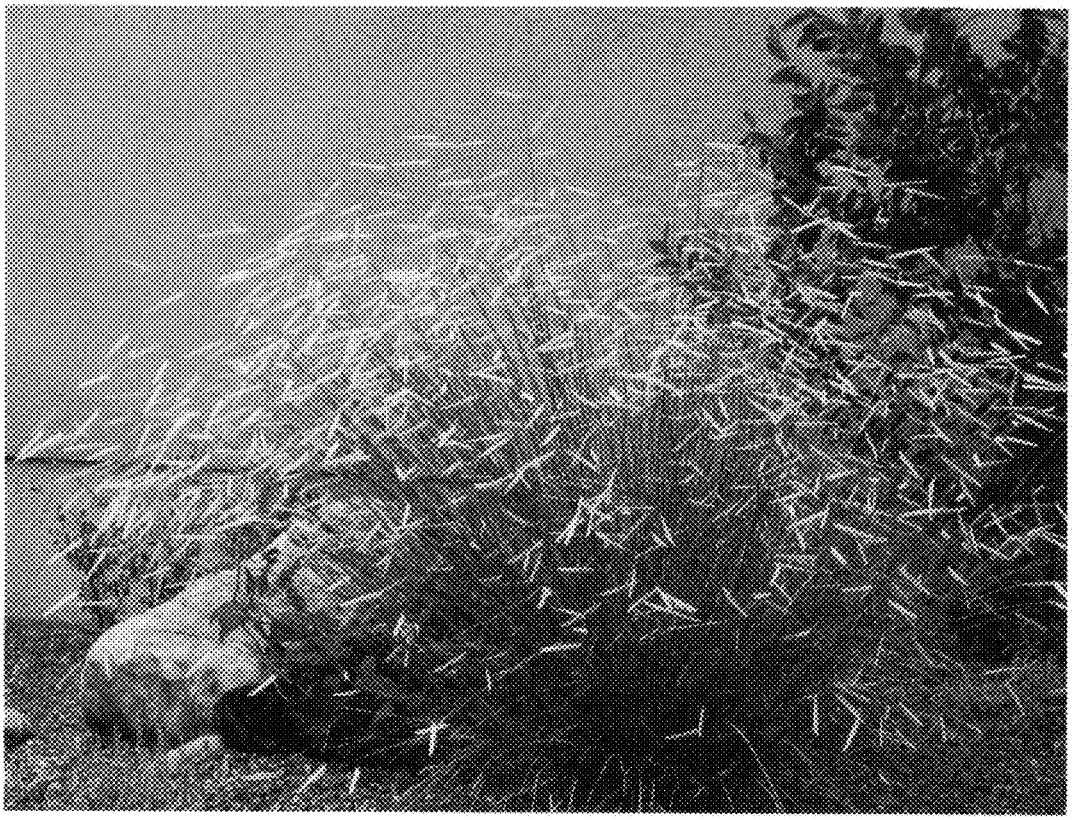
FIG. 1 shows an overall view of a mature grass plant of the present invention taken in September of 2009.
Figure 2:
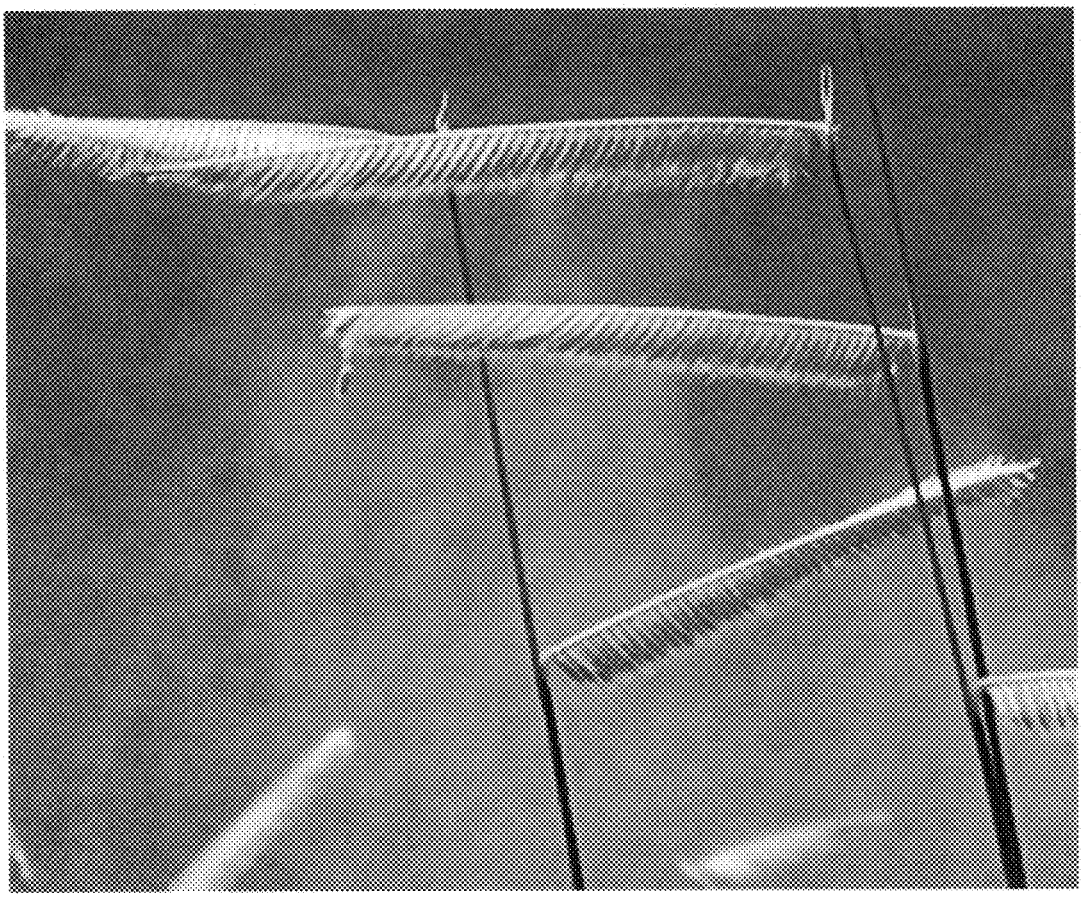
FIG. 2 shows a close-up view of the flower heads of the present invention taken in August of 2009.

The following description of 'Blonde Ambition' is based on observations of live and dried specimens taken in March 2010 in Fort Collins, Colo. The descriptions are of plants approximately two and a half years old. Color references are primarily to the R.H.S. Colour Chart of The Royal Horticultural Society of London (R.H.S.), Fifth Edition (2007).

DETAILED BOTANICAL DESCRIPTION

Classification:
- *Family.*—Poaceae.
- *Botanical.*—*Bouteloua gracilis.*
- *Denomination.*—'Blonde Ambition'.
- *Common name.*—Blue grama grass.

Adaptation: Intermountain west of the United States

Growth:
- *Form.*—Densely tufted, perennial grass.
- *Height.*—30.0 cm to 45.0 cm.
- *Width.*—6.0 cm to 7.0 cm.
- *Habit.*—Erect to decumbent with age.
- *Plant spread (cm).*—5.0 cm to 10.0 cm.
- *Root description.*—Fibrous root system; dense and shallow growth, mat-forming.

Stems:
- *Number of branches per plant.*—10 or more.
- *Length.*—30.0 cm to 45.0 cm.
- *Diameter (measured from the midpoint).*—5.0 cm.
- *Internode length.*—0.5 cm to 2.0 cm.
- *Color.*—RHS 145A.
- *Texture.*—Smooth, glabrous.

Leaf blade:
- *Color.*—RHS 145A on proximal portion and RHS 146A on distal portion or RHS 146A throughout.
- *Length.*—4.0 cm to 45.0 cm.
- *Width.*—0.1 cm to 0.3 cm.
- *Shape.*—Linear.
- *Apex.*—Acute.
- *Base.*—Truncate.
- *Margin.*—Entire, flat.
- *Arrangement.*—Alternate, basal.
- *Culm (not sheath).*—Surface: Glabrous.
- *Leaf hairiness.*—Absent.

*Sheath.*—Length (measured from top of node): 1.5 cm to 4.0 cm. Color: RHS 145A. Hairs: Absent. Keel: Absent.

*Ligules.*—Texture: Ciliate. Length: 0.1 mm to 0.5 mm.

Inflorescence:

*Spike.*—More than one (2 to 3).

*Spikelet.*—Perfect. Color: RHS 161C. Length: 2.5 cm to 5.0 cm. Arrangement: To one side of rachis. Ligule: Hairy.

*Panicle.*—(of 1 to 3 spicate branches). Length (cm): 2.0 cm to 10.0 cm. Color: RHS 161C. Rachis length: 2.5 cm to 5.0 cm.

*Palea.*—Awned.

*Lemma.*—3-awned. Keel: Present. Pubescence: Present (pubescent below on the nerve and the callus densely pubescent).

*Glumes.*—Unequal in size. Shape: Linear to linear and lanceolate. Pubescence: Small hairs present on the nerve, otherwise glabrous. Length: 1.5 mm to 6.0 mm.

Seed: No seeds were observed

Disease and Insect resistance: No special observations made

COMPARISON WITH COMMERCIAL VARIETIES

'Blonde Ambition' differs from the commercial comparison *Bouteloua* variety 'Hachita' (unpatented) in that 'Blonde Ambition' has flower heads that emerge with a distinctive chartreuse color and ages to blonde as the seeds mature while 'Hachita' has flower heads that emerge with a blue-green color and ages to a brown color.

I claim:

1. A new and distinct *Bouteloua* grass plant as described and illustrated herein.

* * * * *